United States Patent [19]

Struck

[11] Patent Number: 4,703,003
[45] Date of Patent: Oct. 27, 1987

[54] MONOCLONAL ANTIBODY WITH A HIGH AFFINITY FOR DIGOXIN

[75] Inventor: Carl-Julius Struck, Wiesbaden, Fed. Rep. of Germany

[73] Assignee: Boehringer Ingelheim KG, Ingelheim am Rhein, Fed. Rep. of Germany

[21] Appl. No.: 640,317

[22] Filed: Aug. 13, 1984

[30] Foreign Application Priority Data

Aug. 20, 1983 [DE] Fed. Rep. of Germany ....... 3330160

[51] Int. Cl.$^4$ .................. C12P 21/00; C12N 15/00; C12N 5/00; C12R 1/91
[52] U.S. Cl. .................................. 435/68; 435/172.2; 435/948; 435/240.27; 530/384; 436/548; 935/104
[58] Field of Search .................. 435/7.68, 172.2, 240, 435/241, 948; 436/548; 424/85; 260/112 R; 935/104; 530/387

[56] References Cited

U.S. PATENT DOCUMENTS 4,477,576 10/1984 Deutsch et al. ..................... 436/500

OTHER PUBLICATIONS

Hunter et al. "High-Affinity Monoclonal Antibodies to the Cardiac Glycoside Digoxin" 1982, J. of Immunology, vol. 129, pp. 1165–1172.
Bäng et al. "Studies of Monoclonal and Polyclonal Anti-Digoxin Antibodies for Serum Digoxin RIA" 1981, Scand J. Clin. Lab. Invest., vol. 41, pp. 75–78.
Zakberg et al. "Monoclonal Antibodies to Drugs-Digoxin" 1983, Int. J. Immunopharmac., vol. 5, pp. 397–402.
Margolies et al. "Monoclonal Antibodies to the Cardiac Glycoside Digoxin" 1981, Res. Monogr. Immunology (3) pp. 367–374.

*Primary Examiner*—Thomas G. Wiseman
*Assistant Examiner*—Elizabeth C. Weimar
*Attorney, Agent, or Firm*—Weissenberger, Hammond & Littell

[57] ABSTRACT

A hybridoma which produces monoclonal antibodies having a high affinity and selectivity for digoxin is produced by immunizing mice with digoxin, fusing the spleen cells from the treated mice with mice myeloma cells, separating hybrids from non-fused cells, selecting the hybrids which produce monoclonal antibodies directed against digoxin and isolating the hybrids.

10 Claims, 6 Drawing Figures

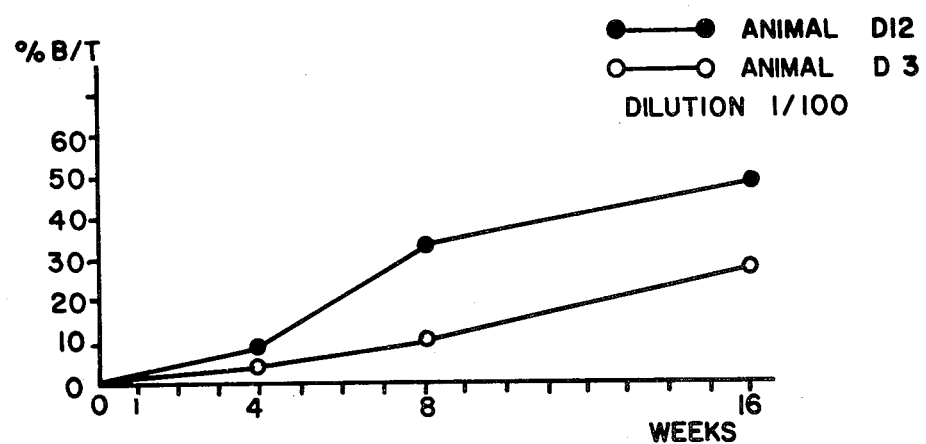
FIG. 1
FIG. 2
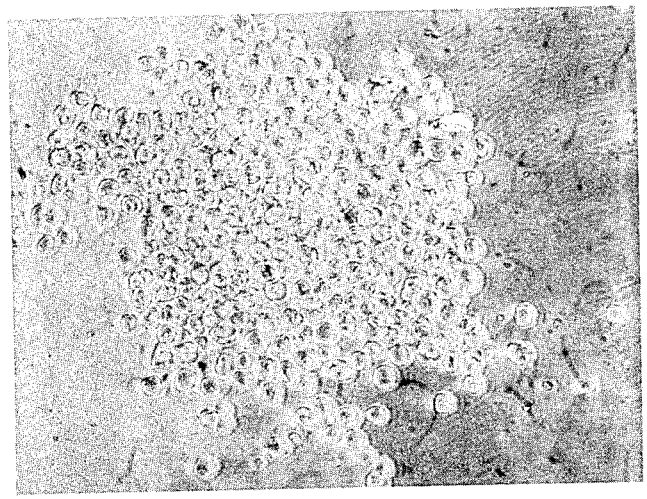

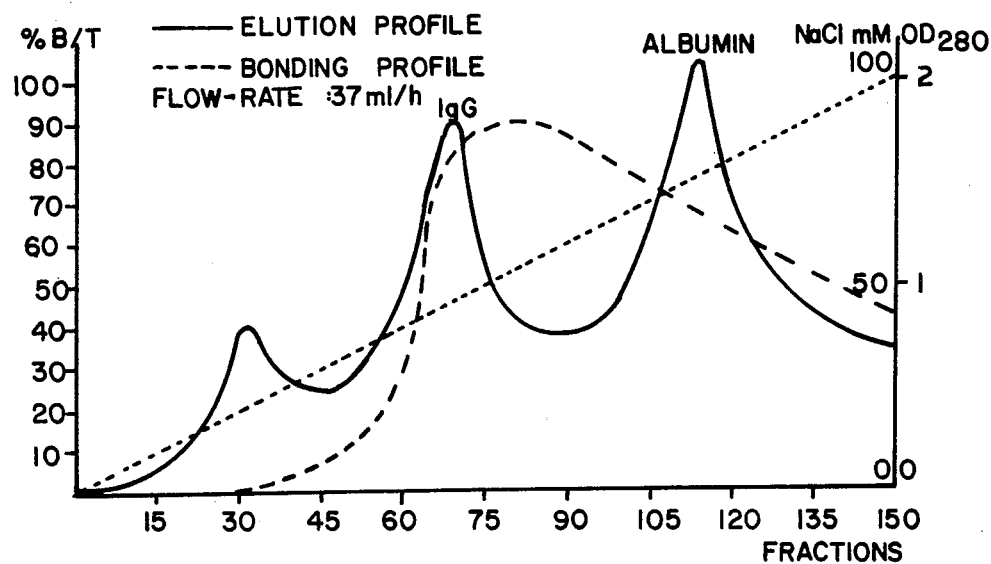
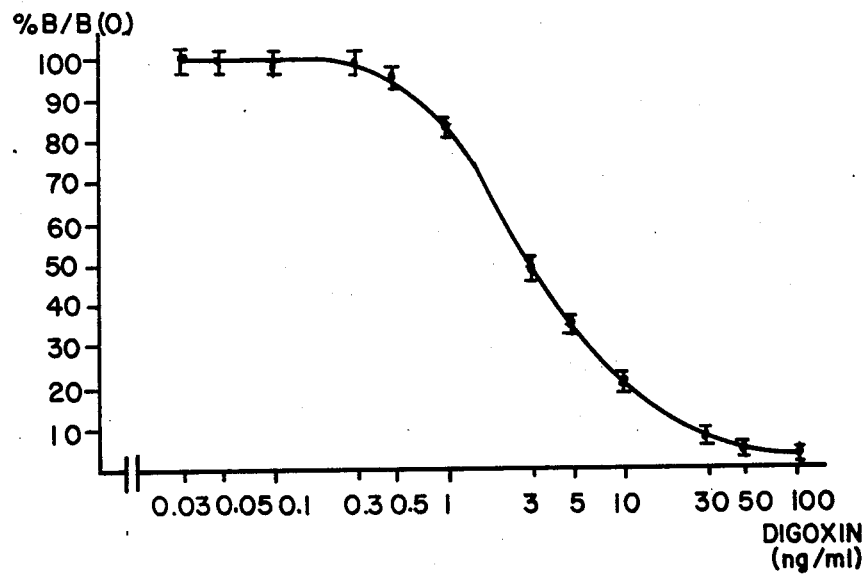

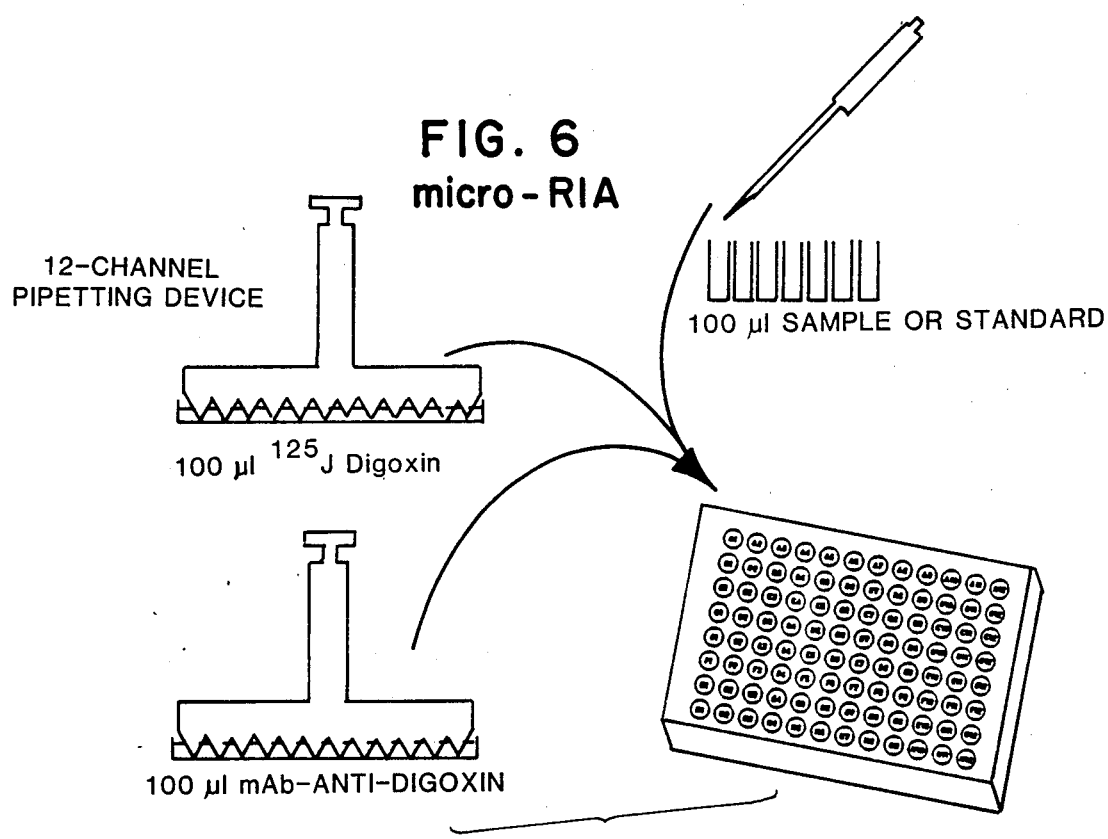
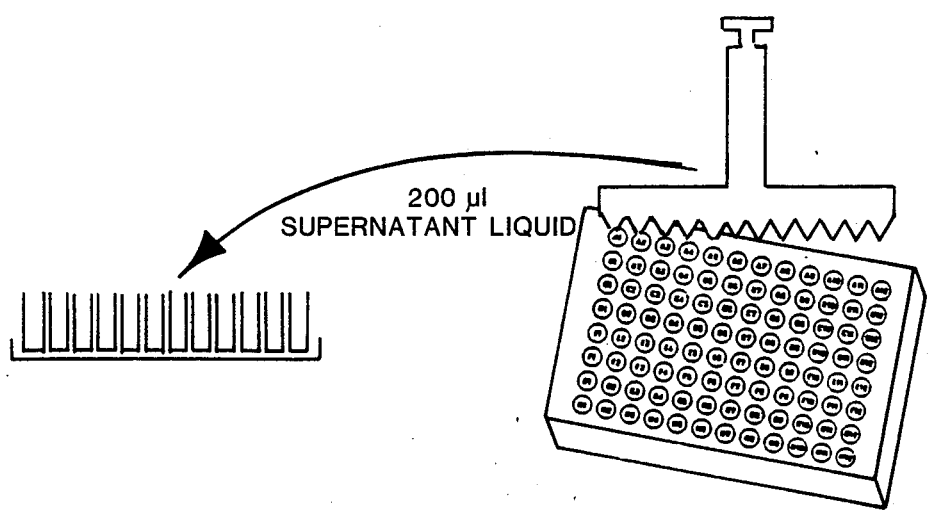

MONOCLONAL ANTIBODY WITH A HIGH AFFINITY FOR DIGOXIN

This invention relates to a monoclonal antibody with a high affinity for the digitalis glycoside digoxin and a low sensitivity to related glycosides and sprionolactone, to the cell lines which produce this monoclonal antibody, to processes for the preparation thereof, to the use of this antibody, and to a test system containing this monoclonal antibody.

BACKGROUND OF THE INVENTION

At present, millions of coronary patients throughout the world are treated with digitalis glycosides [J. R. Ochs, G. Bodem, Med. Welt 30, 602 (1978)]. Thus, this group of preparations are among the drugs most frequently prescribed. Within the entire group, digoxin plays the most important part, having a share of over 90%.

However, the wide distribution and frequent use of the digitalis glycosides should not conceal the fact that these are potentially dangerous substances-their therapeutic range is extremely small. Therefore, in order to achieve an effective and safe therapy, it is essential to monitor the digitalis level continuously. A series of different test procedures have been developed for this purpose wherein the antibodies formed against the glycoside by the body are used as test reagents. These antibodies are obtained from the serum of host animals immunized with digitalis. In this way, antisera of a polyclonal nature are obtained, that is, these sera contain different antibodies.

A major problem, however, in a number of tests for digoxin is the strong cross-reaction with digitoxin, a substance which differs from digoxin only in the presence of an hydroxyl group in 12-position:

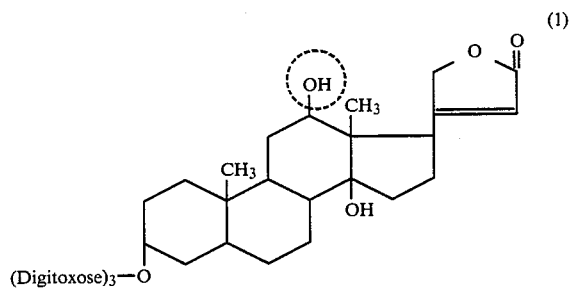

(1)

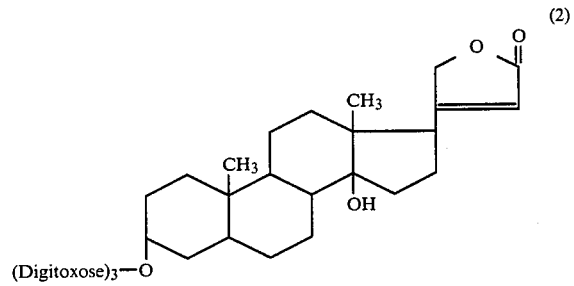

(2)

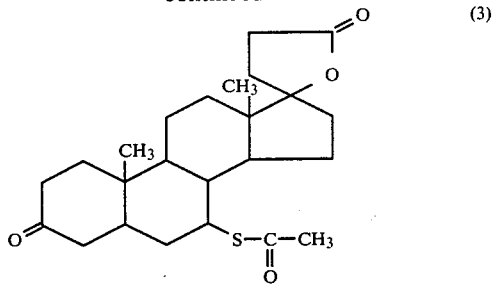

(3)

Structural formulas of (1) digoxin, (2) digitoxin and (3) spironolactone.

However, even more important than a cross-reaction caused by digitoxin, is the possibility of cross-reactive interference, caused by spironolactone (for example, Aldactone ®), an aldasterone antogonist which is frequently administered with digoxin, which occurs in many assays, even commercial ones. This substance is administered in a substantially higher dosage, and if the test is not sufficiently discriminating, it can simulate dangerously high levels.

Attempts have been made, by laborious procedures for purification by affinity chromatography, to improve these cross-reactivities of the antisera which are conventionally produced in rabbits or sheep. However, a disadvantage encountered here is the need for large quantities of antiserum (on account of low purification yields) and the fact that any improvement in the cross-activity is often accompanied by a significant reduction in the detection sensitivity. This is due to the fact that these particular high-affinity antibodies which are responsible for a high sensitivity are very difficult to elute, or even impossible to elute, from the affinity matrix.

As an alternative to the conventional methods of producing antibodies, since the end of the seventies the production of antibodies by hybridoma cell lines in cell culture has become increasingly important, based on the pioneering work of KOHLER and Milstein 1975/76 [Nature, 256, 495 (1975)]. These cell lines are obtained after somatic fusion of spleen cells from a previously immunized mouse with cells of a mouse tumor line and subsequent repeated cloning steps.

Since they can all be traced back to a single parent cell, they are distinguished by the fact that they each produce exclusively only a single type of antibody of uniform specificity, that is, monoclonal antibody (mAK). Moreover, their theoretically unlimited growth as a tumor cell line makes it possible to produce theoretically unlimited quantities of antibody.

For tests for continuously monitoring digoxin-treated patients, or for clearing up cases of poisoning, it is sensible and desirable to use an mAK in the test system precisely because of the typical properties mentioned above.

OBJECTS OF THE INVENTION

The main object of the present invention is to develop, by somatic cell fusion, monoclonal antibodies with high affinity for the digitalis glycoside digoxin. As has already been mentioned, the problem of cross-reaction with other substances is encountered especially in digoxin tests.

Therefore, a further object of the invention is to develop monoclonal antibodies with high affinity for the digitalis glycoside digoxin, characterized in that they have low affinity for related glycosides, particularly digitoxin, and low sensitivity to the aldosterone antagonist spironolactone.

Other objects and advantages of the invention will become apparent as the description thereof proceeds.

THE INVENTION

Antibodies consist of a constant part which is common to all antibodies and a variable polypeptide moiety. The specific properties of an antibody depend only on the variable region. If an organism is stimulated by an antigen to produce antibodies, immunoglobulins are formed which are directed against this antigen. However, since an antigen normally has a number of determinant groups and therefore several points of adhesion for antibodies, a mixture of antibodies is formed which are indeed directed against the same antigen but have different affinity constants and vary in their specificity.

The problem is now to find in this mixture, if possible, those antibodies which combine both properties: high affinity and specificity for digoxin.

All the monoclonal antibodies of the desired sensitivity which have been obtained in the tests heretofore used have the same disadvantages as the antisera of a polyclonal nature: they show affinity for digoxin but no negligible cross-reactivity for digitoxin and/or spironolactone.

The objects of the invention are achieved by fusing the spleen cells of a mouse, obtained after immunization with digoxin, with a mouse tumor cell line in known manner and cultivating these somatic fused cells in a suitable medium, and identifying and selecting, by means of a special screening test, the hybrid cells which produce the desired antibodies, that is, the monoclonal antibodies with a high affinity and sensitivity for digoxin.

For this purpose, identical samples from identical cell culture supernatants were examined for their binding activity toward digoxin on the one hand and toward digitoxin on the other hand by means of a radioimmunoassay. By directly comparing these activities with one another it was possible to select the cell lines which produced highly active mAK in the presence of digoxin but weakly active mAK in the presence of digitoxin. These highly specialized cells were isolated and identified.

The immunization of the mice, isolation of the spleen cells, fusing of the cells, cultivating and selection of the hybrids, sub-cloning of the hybrids which produce the desired antibody, the isolation of the hybrids and of the antibodies were all carried out by processes known to those skilled in the art. Reference is made, for example, to the studies of KOHLER and MILSTEIN, Nature, 256, 495 (1975), HOCHKEPPEL et al., Eur. J. Biochem. 118, 437 (1981) and SECHER et al., Nature 285, 446 (1980).

For the immunization, the person skilled in the art can use the Balb/c mice which are conventionally used. For stabilization and replication of the hybrids, cultivation may be carried out in vitro and in vivo. For the in vivo culture, the hybrids were injected into the abdominal cavity of mice which had previously been treated with a tumor stimulator. The replicated monoclonal antibodies of the desired specificity were then isolated from the ascites liquid and purified if necessary.

I have discovered that this monoclonal antibody according to the invention has a high affinity for digoxin; thus, an essential condition for use in the test system is met.

Unlike in the majority of conventional anti-digoxin sera of a polyclonal nature and also several other monoclonal antidigoxin antibodies described in the literature [YELTON, D. E., SCHARFF, M. D.; Ann. Rev. Biochem. 50, 657–680, (1981); MARGOLIES, N. M.; HUNTER, M. M.; SMITH, T. W. ; NOVOTNY, J.; HABER, E.; in: Monoclonal antibodies and T-cell hybridomas; HÄMMERLING, G. J.; HÄMMERLING, U.; KEARNEY, J. F.; eds.; pp. 367–374 Elseiver, North Holland (1981); BANG, B. E.: HURME, M.: IUNTUNEN, K.: MÄKELA, O.: Scand. J. Clin. Lab. Invest. 41, 75–78 (1981); HUNDER, M. M.: MARGOLIES, M. N. JU, A.: HABER, E.: J. Immunol., 129, 1165–1172 (1982)], the mAK according to the invention has a marked specificity for digoxin. Even a substance which is as similar to digoxin as digitoxin can be clearly distinguished (cross-reaction about 1.3%).

The fact that virtually no cross-section can be detected for other similarly structured substances, for example in the steroid group, has been confirmed. The use of this mAK in therapy monitoring is particularly favored by the extremely low affinity with the aldosterone antagonist spironolactone which is frequently administered in conjunction with digoxin; in this case only a negligibly small cross-reaction of less than 0.007% could be detected.

On the basis of the monoclonal anti-digoxin antibody of this invention, a test system was set up in Microtiter ® plates which not only saved a considerable amount of time but also made it possible to reduce significantly the quantity of reagents required. In particular, the "micro-RIA" (RIA=Radio-Immuno-Assay) design makes it possible to measure nonpretreated plasma samples after the administration of therapeutic doses of digoxin, thanks to its sensitivity (limit of detection: 0.8 ng/ml).

All in all, the test system based on the mAK according to the invention is superior to the kits which are currently commercially available, both in its sensitivity and in its specificity.

The micro-test system means that testing can be usefully carried out as a routine assay. One particular advantage of an RIA based on an mAK is the fact that it would be possible to go back, for a theoretically unlimited period of time, to an antibody source which can produce monoclonal antibodies with constant properties in theoretically unlimited quantities, as a continuously growing cell line, either in a suspension cell culture or in the ascites mouse.

In the attached drawings

FIG. 1 shows the increase in antibody production for two animals.

FIG. 2 is a microscopic picture of the cell clones after ten days' growth.

FIG. 3 shows the elution profile of ascites liquid in purification by affinity chromatography (using DEAE Affi Gel Blue ®).

FIG. 4 shows the sensitivity of digoxin-RIA when using the mAK D 50 ("micro-RIA" system). Average values (±standard deviation) from a four-fold measurement (mAK dilution 1:40,000, T=6,000 cpm, bo=40%, NSB=1.7%).

Figure 5:
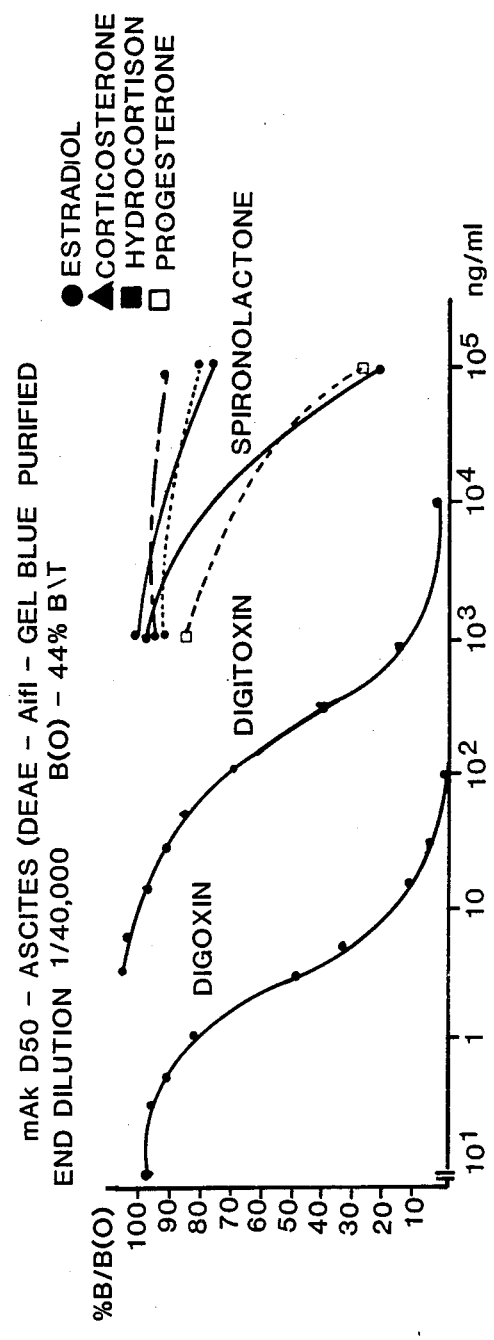
FIG. 5 shows the interference of similarly structured substances in the digoxin micro-RIA.

FIG. 6 shows the sequence steps of the "micro-RIA". The individual steps are described in detail in section 1.9.2 (method). Summary: 100 μl of sample or digoxin standard are pipetted, like 100 μl $^{125}J$ digoxin and 100 μl anti-digoxin mAK, into the depressions in a Microtiter ® plate. After incubation at room temperature, the bound and free radioactivity is separated by means of dextrane active charcoal. The bound radioactivity is determined using aliquots of the individual mixtures.

The following example illustrates the present invention and will enable others skilled in the art to understand it more completely. It should be understood, however, that the invention is not limited solely to the particular example given below.

1. METHOD

1.1 Preparation of the Immunogen

The immunogen conjugate consisting of digoxin as the hapten and bovine serum albumin (BAS, MILES) as the carrier molecule was prepared using the method described by BUTLER & CHEN, Proc. Nat. Acad. Sci. (USA) 57, 71–78 (1967).

1.2 Immunization of the Donor Mice

Only mice of the Balb/c strain were used for immunization, and groups of 20 animals were immunized. Each mouse was given 200 μl of an emulsion of digoxin-BSA and Complete Freud's Adjuvans (CFA, DIFCO Laboratories) by the intraperitoneal route in a ratio of 1:3 (20–50 μg of immunogen per animal).

After four weeks they were given a booster injection of 20–50 μg of digoxin-BSA in 0.9% NaCl. If necessary, this booster injection was repeated several times at four-week intervals.

The immune reaction of the mice was monitored by regular blood samples (Pl. retroorbitalis). In order to determine the antibody titre in the whole blood, reagents from a commercial RIA kit (DIAGNOSTIC PRODUCTS Corp.) were used.

1.3 Culture of the Mouse Tumor Cell Line

The cell line X63.AG8-653 [Kearney et al., J. Immunol. 123, 1548 (1979)] was used as the fusion partner. The cells were stored in freezing medium (see Annex 1) at −196° C. in liquid nitrogen. One week before the fusion, an aliquot was thawed and placed in a plastic Petri dish (10 cm in diameter, Greiner) in RPMI 1640 cell culture medium (see Annex 1). For fusion, the cells were used in the logarithmic growth phase.

1.4 Somatic Cell Fusion

The spleen of an immunized mouse was taken three to four days after the last booster injection under sterile conditions. By carefully triturating it on a stainless steel screen (pore size 100 um) the spleen cells were isolated from the connective tissue and were taken up in PBS (phosphatebuffered salt solution, see Annex 1). The cells were washed twice in DPBS (Dulbecco's PBS, see Annex 1) (centrifuging at 1,000 rpm for 5 min.) and were then taken up in DPBS. The spleen cells and Ag8 cells were mixed at a ratio of 2 to 1 in this mixture. Fusion of the cell populations was started by adding a polyethyleneglycol-DPBS (PEG 4000 71%, DMSO 6% in Dulbecco's PBS; supplied by ROTH/SIGMA/SEROMED). After one minute the PEG was diluted by the addition of Dulbecco's PBS (DPBS, see Annex 1). The cell suspension was washed until all the PEG had been removed and was then taken up, at a density of about $10^6$ cells/ml, in hypoxanthine/aminopterine/thymidine selection medium (Littlefield's HAT medium, see Annex 1). Only fused cells survived in this selection medium, but not the unfused spleen cells or the Ag8 cells which were still contained in the suspension.

1.5 Culture of Hybridoma Cells

The cell suspension after fusion (in HAT medium) was pipetted in 200 μl aliquots into the 96 cavities of Microtiter ® plates (COSTAR type 3596). At 37° C. and at a relative humidity of 95%, the cultures were incubated in an atmosphere of 93% air and 7% $CO_2$ without any change of medium for 7–10 days in an aerated incubator. The cell growth was regularly monitored during this time.

After two to three weeks positive cultures, that is, cultures producing immunoglobulins of the desired specificity, were identified by means of a special screening test developed for this purpose (see section 1.9). At the same time the step-by-step conversion of the cultures from HAT medium through HT medium (see Annex 1) to RPMI 1640 medium was also begun.

1.6 Cloning of Hybridoma Cell Cultures

Positive proliferating cultures were expanded in larger culture vessels (COSTAR cell culture plates type 3524 or 3506). The subsequent cloning was carried out by the "limiting dilution cloning" method. In this method, the suspension of a positive culture is diluted to such an extent that statistically, for each new culture started, 10 or 1 cell, respectively, is inoculated. After 8–12 days, macroscopic colonies are already visible which are derived from single cells. To ensure that real monoclonal cultures are growing, cultures derived from a single common parent cell, the cloning step is carried out at least twice.

1.7 Expansion of Hybridoma Cell Cultures

1.7.1 Expansion in the Cell Culture (in vitro)

About $10^3$ cells were disseminated in 10 ml of RPMI 1640 in Petri dishes (10 cm in diameter, GREINER). Alternatively, cell culture bottles may also be used. The cell-free supernatant contained, after a few days, the mAK secreted by the cells. It could be used directly in the RIA.

1.7.2 Expansion in the ascites mouse (in vivo)

Balb/c mice were given 0.5 ml of the mineral oil Pristan ® (ROTH) by the intraperitoneal route in order to condition the peritoneum. S006-887.

Over a period of 7 to 60 days, a suspension of $10^6$–$10^7$ hybridoma cells per animal in PBS was administered by the intraperitoneal route to the animals thus pretreated. After 8 to 10 days a cannula was passed into the peritoneum, and the ascites liquid containing cells was collected.

The cellular constituents were separated from the ascites liquid by centrifuging (1,000 rpm, 10 min.). The supernatant fraction, which also contained the monoclonal antibodies, was subsequently frozen at −70° C. in aliquots (after dilution, if necessary) or purified by affinity chromatography.

1.8 Purification of the Ascites Liquid

Purification was carried out by using the method of Bruck et al., J. Immunol. Meth. 53, 313–319 (1982).

1.8.1 Pretreatment of the Ascites Liquid

Ascites liquid was centrifuged for 5 minutes at $1000 \times g$ in order to precipitate any cellular constituents. The cell fragments and fibrin aggregates were separated by ultra-centrifuging at $100,000 \times g$ for 30 min. The supernatant fraction was then dialyzed overnight with 100 times the volume of Tris-HCl buffer, 0.02 m/l, pH 7.2. Then further centrifuging was carried out at $10,000 \times g$ for 15 minutes.

1.8.2 Chromatography

A 1 ml aliquot of the pretreated ascites liquid was applied to a column packed with DEAE-Affi-Blue ® (BIO-RAD) (bed volume: 7 ml). The column was washed with 20 ml of column buffer (ris-HCl, 0.02 m/l, pH 7.2). The different proteins were eluted with an NaCl gradient (0–100 mmol/l) at a flow rate of 30–40 ml/h. Fractions of 1–2 ml were collected. The protein content of the individual fractions was constantly monitored during elution. Those fractions which contained antibodies were combined and stored at 4° C. after the addition of 0.02% $NaN_3$.

1.9 Screening Tests for Detecting Antibodies in Whole Blood, Cell Culture Supernatant Fractions and Ascites Liquid Two different methods of finding antibodies in cell culture supernatant fractions were used in the course of the development of the mAK against digoxin: a solid-phase enzyme immunoassay and a radio immunoassay. The latter proved to be particularly suitable for selecting mAK with a low cross-reaction with digitoxin already at the screening stage.

1.9.1 Solid-phase Immunoassay

Preparation of the ELISA Plates

The routine screening test for antibody production was carried out as a solid phase enzyme immunoassay (sp-ELISA) (ELISA=enzyme labelled immunosorbent assay). The 96 depressions in a Microtiter ® plate were first coared with the same digoxin-BSA conjugate used as an immunogen in the immunization (51 μg/hole) and incubated at 37° C. for 90 minutes. The free unspecific binding sites remaining in the plastic surface were blocked with bovine serum albumin (BSA) (0.5% BSA, 0.05% Tween 20, 0.02% $NaN_3$ in PBS). After being washed three times with saline solution (0.15 m NaCl, 0.05% Tween 20, 0.02% $NaN_3$ in double-distilled water) the plates thus pretreated were stored in a moist chamber at 4° C. for up to 4 weeks.

ELISA procedure

One aliquot of each cell culture supernatant fraction was pipetted into each cavity of a previously coated plate. After incubation for 90 minutes at 37° C., the contents of the holes were discarded, and the plate was washed three times with saline solution.

In order to detect the antibody which may be bond to the antigen (digoxin-BSA) and hence to the solid phase from the cell culture supernatant fraction, a second antibody (goat anti-mouse immunoglobulin, anti-MIg, made by MEDAC, 0.25 μg/hole) was used which was labeled with alkaline phosphatase as a detecting reagent. After further incubation (90 min., 37° C.) the enzyme reaction was started by the addition of phosphatase substrate (disodium salt of p-nitrophenylphosphate, SIGMA, 0.1% in diethanolamine buffer, pH 9.0, 100 μl/hole). After about one hour at room temperature a significant yellow coloration could be seen in those cavities in the plate which contained the cell culture supernatant fractions from positive cultures. By using an 8-channel photometer (Titertek Multiskan, made by FLOW Laboratories) compatible with the Microtiter ® System the color reaction could be quantified directly in the plate.

1.9.2 Radioimmunoassay for Screening for Antibody Production

The screening RIA was carried out as "Micro-RIA" (see below) in Microtiter ® plates. A mixture consisted of:

100 μl of cell culture supernatant
100 μl of 125 I-digoxin tracer (DIAGNOSTIC PRODUCTS) or
100 μl of 125 I-digoxin tracer (DIAGNOSTIC PRODUCTS)
100 μl of normal human plasma (MAINZ bloodbank).

After incubation at room temperature (30–45 minutes) the free radioactivity and the radioactivity bound to the antibody were separated by the addition of 50 μl of a suspension of dextrane coated charcoal (MERCK) in phosphate buffer and subsequent centrifuging, $1500 \times g$ for 10 minutes. The bound radioactivity (in the supernatant) was measured in a gamma scintillation counter (KONTRON MR 480C) by means of an aliquot taken from each hole in the Microtiter ® plate.

1.10 Radioimmunoassay for Digoxin

The digoxin RIA was carried out as "micro RIA" in Microtiter ® plates, like the screening test described above under 3.9.2. A mixture in this case consisted of:
100 μl of anti-digoxin mAK
100 μl of 125 I-digoxin tracer
100 μl of plasma sample
100 μl of digoxin standard in plasma.

The pipetting steps (with the exception of pipetting the individual samples or standards) were carried out with 8- or 12-channel pipettes (TITERTEK ®, made by FLOW Laboratories).

All the incubation periods and other operations were the same as for the screening RIA.

1.11 Determination of the Immunoglobulin Sub-class of the mAK

The mAK was characterized more fully in a solid-phase ELISA system.

The cavities in a Microtiter ® plate were coated with antigen (digoxin-BSA). After incubation of the plate thus prepared with the mAK (2 hours at 37° C.) from the cell culture, a second incubation step (1 hour at 37° C.) was carried out with anti-mouse immunoglobulins of various classes and sub-classes and with various classes of light and heavy immunoglobulin chains. In a further step, an enzyme-labeled goat-rabbit immunoglobulin was added. After 1 hour of incubation, the enzyme reaction was started by the addition of p-nitrophenylphosphate.

2. RESULTS

2.1 Immune Response in the Mouse

Four weeks after immunization, the production of anti-digoxin antibodies could be detected by radioimmunology in whole blood in 13 animals out of a group of 20. Only those animals which were found to be particularly immune-reactive were used as spleen donors for the subsequent fusion experiments.

The increase in antibody production is exemplified for two animals in FIG. 1.

2.2 Establishment of the Hybridoma Cell Lines

Exclusively the cell line P3X63.Ag8-635-Th was used as the fusion partner. With this cell line, fusion frequencies (percentage of the cell population surviving in the HAT selection medium) of 50–80% can regularly be achieved (Table I).

TABLE I

| Fusion Number | Number of proliferating colonies after HAT selection | Fusion frequency | Number of colonies with specific antibody secretion | Established Hybridoma |
|---|---|---|---|---|
| 17 | 314 | 81.7% | 1 | 1 |
| 20 | 299 | 52.0 | 3 | 1 |
| 28 | 448 | 77.8 | 6 | 1 |

TABLE I

Summary of the fusion yield in three fusion experiments taken as an example. Fusion 17: 384 cultures originally started; fusion 20 and 28: 576 original cultures.

Those colonies which showed stable growth and antibody production were cloned by the "limiting dilution cloning" method, i.e. the cells of a culture were diluted after fusion and placed in 2 Microtiter ® plates (192 individual cultures), so that statistically there was only one cell in each new culture vessel.

After 10 days, the first cell clones could be detected macroscopically in individual holes in the plates. At this stage the regular and uniform growth could readily be watched under the microscope (FIG. 2).

The production of anti-digoxin antibodies by the individual clones as monitored at regular intervals of one week, first by using solid-phase ELISA and later by means of RIA.

Clones which constantly produced antibodies over a period of several weeks were expanded by two different methods. First, suspension cell cultures were placed in larger Petri dishes or cell culture bottles (in vitro system).

Secondly, the hybridoma clones were propagated as an ascites tumor in the peritoneum of mice which had been pretreated with Pristan ® (in vivo system).

An aliquot of the cell suspension was frozen for storage.

2.3 Production of mAK in Cell Culture and Ascites Mouse

The genetic stability of the cell lines, and hence their ability to produce the desired monoclonal antibody, was monitored over a fairly long period in both systems by constantly checking the antibody titre by means of RIA. It was found that only a relatively small number of clones were stable in this sense. The genetic instability of the majority of clones was shown by the fact that the antibody titer decreased constantly after a few weeks, and thus the ascites liquid or the cell culture supernatant had to be made more concentrated in order to obtain the same bonding of the radioactive tracer in the RIA.

The mouse in which the hybridoma line was growing as an ascites tumor also releases various substances, particularly proteins and hence immunoglobulins and some disruptive enzymes (for example, proteases) into the ascites liquid.

These components cause problems during later use in the test system and therefore it is desirable to purify the ascites liquid.

2.4 Purification of the Ascites Liquid

The ascites liquid was purified by affinity chromatography using DEAE Affi Gel Blue ®.

During the elution with an NaCl gradient (0–100 mmol/l) the IgG fraction was separated from any disruptive proteases (which are only eluted at NaCl concentrations of above 120 mmol/l) and from albumin (FIG. 3).

The monoclonal anti-digoxin antibody was eluted in the IgG peak at 35–50 mmol/l of NaCl. The peak fractions (64–70) had a protein concentration of 80 µg/ml. Using a protease test kit (BIO RAD), it was possible to demonstrate that the fractions of the IgG peak were free from contaminated proteases.

In a binding assay (RIA) it was found that the fractions with the highest protein concentration in the IgG peak cannot necessarily be equated with those which have the highest affinity for a radioactive digoxin tracer.

2.5 Properties of mAK for Digoxin

2.5.1 Immunoglobulin Sub-Class

The anti-digoxin antibody mAK D28-A91-16-B64 (D50 for short) is an immunoglobulin of sub-class IgG$_1$; the light chains can be classified as kappa type.

2.5.2 Affinity

For mAK D28A91-16-B64 the affinity constant for bonding to digoxin was determined using data from radio immunoassays. The results of these investigations and the comparisons with the polyclonal antibodies of two commercial RIA kits are assembled in Table 2.

TABLE II

| Bonding reagent | $K_a^{-1}$ [molar$^{-1}$] |
|---|---|
| mAK D50 | $4.1 \times 10^9$ |
| AS Diagnostic Products | $6.0 \times 10^9$ |
| AS Becton-Dickson | $4.1 \times 10^9$ |

TABLE II

Comparison of the $K_a$ values of mAK D50 with the data given for antisera from commercial kits. The affinity constant of the mAK for digoxin was determined using RIA measured data.

The $K_a$ values shown indicate that the anti-digoxin mAK is a high-affinity antibody. The affinity constant corresponds in its order of magnitude to the values known from polyclonal antisera.

2.5.3 Sensitivity

In order to determine the sensitivity of the RIA system based on the mAK D50, digoxin standards are measured in quadruplicates over a concentration range of from 0.03 ng/ml to 100 ng/ml (FIG. 4). The detection limit (in "micro-RIA") is significantly below 1 ng/ml. The high affinity of mAK for digoxin is reflected in this.

2.5.4 Specificity

As can be seen from FIG. 4, only very slight fluctuations are found for the values of the replicates in multiple measurements. As an example of the reproducible accuracy of the assay, Table 3 shows the data from which the standard curve in FIG. 4 was derived, together with the values for the absolute and relative standard deviations.

TABLE III

| Digoxin [ng/ml] | % b/b (c) | Absolute standard deviation | Relative standard deviation |
|---|---|---|---|
| 0.03 | 99.24 | 2.35 | 2.37% |
| 0.05 | 98.53 | 3.03 | 3.08% |
| 0.1 | 97.13 | 1.93 | 1.99% |

TABLE III

Precision of the digoxin "micro-RIA" (for the test parameters see FIG. 4).

Especially when an anti-digoxin antibody is used in the test system (for instance for monitoring therapy), it is critically important how well the antibody can distinguish digoxin from similar substances which are in some cases endogenic in the body (such as steroids) or are administered together with the digoxin medication (for example spironolactone as an aldosterone antagonist).

It is also desirable to be able to distinguish clearly between digoxin and digitoxin; the former differs from the latter only by the presence of an OH-group in the 12-position of the steroid ring system.

The mAK D28-A91-16-B64 shows exceptional specificity for digoxin in the "micro RIA" (FIG. 5). The cross-reaction with digitoxin is 1.3%, while the cross-reaction with spironolactone is 0.007%. Similarly, the various steroids tested show only slight interference (FIG. 5).

The cell line MAK D50 (D28-A91-16-B64) was deposited on Dec. 21, 1983 under the number I-272 at the "Collection nationale de cultures de microorganismes (C.N.C.M.), Institut Pastuer, Paris" in accordance with Rule 28 of the European Patent Convention.

2.4.5 "Micro RIA" for Determining Digoxin

The microtiter system proved exceptionally suitable in the screening test. The possibility of transferring cell culture supernatant fractions into test plates with the same grid subdivisions permits the use of special pipetting apparatus (12-channel pipettes) resulting in a substantial reduction in the labor and time required.

In the light of the good experience of the screen assay, the advantages of the microtiter grid system were also used for the digoxin test itself. The RIA, which was originally carried out in conventional RIA test tubes (plastic reagent tubes, 75×12 mm, SARSTEDT), was adapted to the requirements of the microtiter system.

For this purpose, the assay volume was reduced to 300 μl. The separation of the bound radioactivity from the free radioactivity was made possible by a suitable concentration of the active charcoal suspension which, moreover, did not exceed a volume of 50 μl to be pipetted during use.

An useful RIA system was obtained by that. The operation of the system is diagrammatically shown in FIG. 6. All RIA data of this report (standard curve, evidence of specificity, etc.) were obtained using this assay system. In addition to the significant saving of working time (about 300 samples per hour can be processed in the "micro-RIA"), the small assay volume also reduces the quantities of reagents needed.

ANNEX 1

Compositions of buffer solutions and culture media which were employed:

1. Buffer solutions 1.1 Dulbecco's PBS (DPBS, quantities in mg/l).
Literature: EARLE, W. R. et al., J. Nat. Cancer. Inst. 4, 165 (1943). HANKS, J. H. and R. E. WALLACE, Proc. Soc. Exp. Biol. Med. 71, 196 (1949).
DULBECCO, R. and M. VOGT, J. Exp. Med. 99, 167 (1954).

|  | PBS (DULBECCO) | EARLE's Salts | HANKS' Salts |
|---|---|---|---|
| NaCl | 8000 | 6800 | 8000 |
| KCl | 200 | 400 | 400 |
| $Na_2HPO_4$ | 1150 | — | 48 |
| $NaH_2PO_4.H_2O$ | — | 140 | — |
| $KH_2PO_4$ | 200 | — | 60 |
| $MgCl_2.6\ H_2O$ | 100 | — | —* |
| $MgSO_4.7\ H_2O$ | — | 200 | 200* |
| $CaCl_2$ | 100 | 200 | 140 |
| Glucose | — | 1000 | 1000 |
| Phenol red | — | 10 | 10 |
| $NaHCO_3$ | — | 2200 | 350 |

*In the original composition, there are 100 mg/l of $MgCl_2.6\ H_2O$ and 100 mg/l of $MgSO_4.7\ H_2O$.

1.2 Phosphate buffer (PBS, amounts in g/l)

| 9.6 mM, pH = 7.4 | |
|---|---|
| NaCl | 8.0 |
| KCl | 0.2 |
| $Na_2HPO_4.2\ H_2O$ | 1.44 |
| $KH_2PO_2$ | 0.2 |

1.3 Sodium bicarbonate buffer 0.1 mol/l $Na_2HCO_3$ in double-distilled water with 0.1 mol/l of $NaCO_3$ in double-distilled water adjusted to pH 9.0.

1.4 Sodium acetate buffer (0.1 mol/l)

8.203 g $CH_3COONa$ in 800 ml $H_2O$
29.22 g NaCl
adjusted to pH 4.0 with acetic acid up to 1 liter of double-distilled water.

1.5 Glycine HCl buffer (0.1 mol/l)

Solution a: 0.1 mol/l glycine (7.505 g/l)+0.1M NaCl (5.86 g/l)
Solution b: 0.1 mol/l HCl
Composition of buffer:
  88% solution a
  12% solution b
  pH 3.2.

1.6 Saline wash solution (for ELISA)

0.15 mol/l NaCl
0.05% Tween 20
0.02% $NaN_3$
in double-distilled water.

1.7 Blocking buffer (for ELISA)

0.5% HSA
0.05% Tween 20 in PBS
0.02% $NaN_3$

1.8 Diethanolamine buffer (for ELISA)

48 ml of diethoanolamine
24.5 mg $MgCl_2$ (52.26 mg $MgCl_2.6H_2O)l_2.6H_2O$)
400 ml of double-distilled water
adjust to pH 9.0 with 1 mol/l of HCl and make up to 500 ml of double-distilled water.

2. Polyethyleneglycol solution (for fusion)

20 g of PEG 4000
autoclave for 20 minutes (121° C.)
cool to 80° C.
add 28 ml of DPBS (with 15% DMSO).

3. Cell culture media

3.1 Medium RPMI 1640 (amounts in mg/l)

Literature:
MOORE, G. E. et al.,
J. Am. Med. Assoc. 199, 519 (1967.

| | |
|---|---|
| NaCl | 6000 |
| KCl | 400 |
| $Na_2HPO_4.7 H_2O$ | 1512 |
| $MgSO_4.7 H_2O$ | 100 |
| $Ca(NO_3)_2.4 H_2O$ | 100 |
| D-Glucose | 2000 |
| Phenol red* | 5 |
| $NaHCO_3$ | 2000 |
| L-Arginine | 200 |
| L-Asparagine | 50 |
| L-Aspartic Acid | 20 |
| L-Cystine | 50 |
| L-Glutamine | 300 |
| L-Glutamic acid | 20 |
| Glycine | 10 |
| L-Histidine | 15 |
| L-Hydroxyproline | 20 |
| L-Isoleucine | 50 |
| L-Leucine | 50 |
| L-Lysine-HCl | 40 |
| L-Methionine | 15 |
| L-Phenylalanine | 15 |
| L-Proline | 20 |
| L-Serine | 30 |
| L-Threonine | 20 |
| L-Tryptophane | 5 |
| L-Tyrosine | 20 |
| L-Valine | 20 |
| Glutathione | 1 |
| Biotin | 0.2 |
| Vitamin $B_{12}$ | 0.005 |
| D-CA-Pantothenate | 0.25 |
| Choline chloride | 3 |
| Folic acid | 1 |
| i-Inosite | 35 |
| Nicotinamide | 1 |
| p-Aminobenzoic acid | 1 |
| Pyridoxine.HCl | 1 |
| Riboflavin | 0.2 |
| Thiamin.HCl | 1 |

Liquid medium contains 10 mg/l of phenol red additionally:

| | |
|---|---|
| 0.002 mol/l | L-glutamine |
| $10^5$ U/l | Penicillin-streptomycin |
| $2 \times 10^{-5}$ mol/l | Mercaptoethanol |
| 10–15% | FCS |

3.2 HAT medium/HT medium

A: Aminopterine 3.82 mg/200 ml of double-distilled water.
HT: Hypoxanthine 272.20 mg in 200 ml of double-distilled water
Thymidine: 76.50 mg
HAT medium: 10 ml of basic solution A + 10 ml of basic solution HT on 1000 ml of RPMI 1640 (complete with additives).
HT medium: 10 ml of basic solution HT on 1000 ml of RPMI 1640 (complete with additives).

3.3 Freezing medium

70% DPBS
10% DMSO (dimethylsulfoxide)
20% FCS (Fetal Calves' serum).

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

I claim:

1. A hybridoma which produces monoclonal antibodies having a high affinity and selectivity for digoxin, a cross-reactivity of less than 1.3% with digitoxin and a cross-reactivity of less than 0.007% with spironolactone.

2. A hybridoma of claim 1 produced by immunizing mice with digoxin and carrying out selection of the hybrid cells with digoxin, digitalis glycosides and spironolactone.

3. A hybridoma of claim 2 which is produced by using digitoxin as the digitalis glycoside.

4. A monoclonal antibody having a high affinity and specificity for digoxin, a cross-reactivity of less than 1.3% with digitoxin and a cross-reactivity of less than 0.007% with spironalactone.

5. A monoclonal antibody of claim 4 which is prepared by immunizing mice with digoxin, carrying out the selection of the hybrid cells with digoxin, digitalis glycosides and spironolactone, and isolating the monoclonal antibody.

6. A monoclonal antibody of claim 5 which is produced by using digitoxin as the digitalis glycoside.

7. The method of producing a hybridoma of claim 1, which comprises
   (a) immunizing mice with digoxin,
   (b) fusing the spleen cells from the treated mice with mouse myeloma cells,
   (c) separating hybrids from non-fused cells,
   (d) selecting the hybrids which produce monoclonal antibodies directed against digoxin by using digoxin, digitalis glycosides and sprionolactone, and
   (e) isolating the hybrids.

8. The method of claim 7 where digitoxin is used as the digitalis glycoside.

9. The method of producing a monoclonal antibody of claim 4, which comprises
   (a) immunizing mice with digoxin,
   (b) fusing spleen cells from the treated mice with mouse myeloma cells,
   (c) separating hybrids from non-fused cells,
   (d) selecting the hybrids which produce monoclonal antibodies directed against digoxin by using digoxin digitalis glycosides and spironolactone, and
   (e) isolating the monoclonal antibodies after the growth of the cells in vivo or in vitro.

10. The method of claim 9, where digitoxin is used as the digitalis glycoside.

* * * * *

UNITED STATES PATENT AND TRADEMARK OFFICE
CERTIFICATE OF CORRECTION

PATENT NO. : 4,703,003

DATED : October 27, 1987

INVENTOR(S) : Carl Julius Struck

It is certified that error appears in the above-identified patent and that said Letters Patent is hereby corrected as shown below:

Column 8, line 37: "100 $\mu$l" should read -- or 100 $\mu$l --.

Column 10, line 17: "fractions (64-70)" should read

-- fractions (65-70) --.

Signed and Sealed this

Twenty-third Day of August, 1988

*Attest:*

DONALD J. QUIGG

*Attesting Officer*   *Commissioner of Patents and Trademarks*